United States Patent [19]

Mrozik et al.

[11] Patent Number: 4,831,016

[45] Date of Patent: May 16, 1989

[54] REDUCED AVERMECTIN DERIVATIVES

[75] Inventors: Helmut Mrozik, Matawan; Thomas L. Shih, Edison, both of N.J.

[73] Assignee: Merck & Co., Inc., Rahway, N.J.

[21] Appl. No.: 925,772

[22] Filed: Oct. 31, 1986

[51] Int. Cl.$^4$ .............................................. A61K 31/35
[52] U.S. Cl. ................................. 514/30; 514/450; 549/214; 549/264; 536/7.1
[58] Field of Search ............... 549/264, 214; 536/7.1; 514/30, 450

[56] References Cited

U.S. PATENT DOCUMENTS 4,530,921 7/1985 Mrozik ............................ 549/264

Primary Examiner—Glennon H. Hollrah
Assistant Examiner—A. A. Owens
Attorney, Agent, or Firm—David L. Rose; Michael C. Sudol

[57] ABSTRACT

There are disclosed novel avermectin reduction products. The compounds are prepared by selective catalytic hydrogenation of avermectin-like compounds or by reaction of selected double bonds with electrophylic reagents. The reduced avermectin compounds have utility as anti-parasitic agents and compositions for that use are also disclosed. The compounds are also highly potent insecticides against agricultural pests. The reduced avermectin compounds have increased stability towards light which prolongs their insecticidal activities when applied to field crops subject to irradiation by sunlight.

11 Claims, No Drawings

REDUCED AVERMECTIN DERIVATIVES

BACKGROUND OF THE INVENTION

The term avermectin (previously referred to as C-076) is used to describe a series of compounds isolated from the fermentation broth of an avermectin producing strain of Streotomyces avermitilis and derivatives thereof. The morphological characteristics of the culture are completely described in U.S. Pat. No.4,310,519. The avermectin compounds are a series of macrolides, each of which is substituted thereon at the 13-position with a 4'(α-L-oleandrosyl)-α-L-oleandrose group. The avermectin compounds and the instant derivatives thereof have a very high degree of anthelmintic and anti-parasitic activity.

Also included in the prior art are certain synthetically modified avermectins such as 22,23-dihydro avermectin B1a/B1b also known as ivermectin disclosed in U.S. Pat. No. 4199569.

The avermectin series of compounds, which are isolated from a fermentation broth, have the following structure:

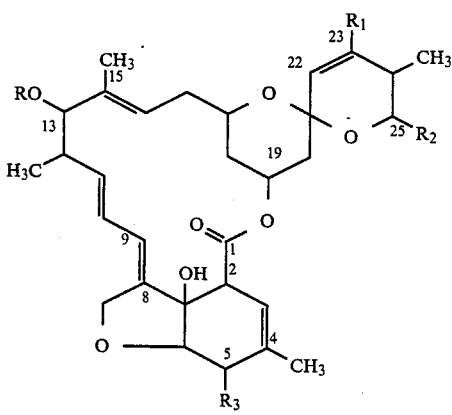

wherein R is the 4'-(α-L-oleandrsyl)-α -L-oleandrose group of the structure:

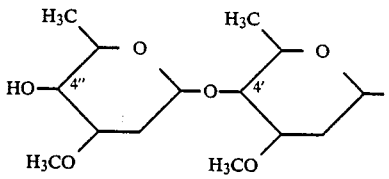

and wherein the broken line indicates a single or a double bond; $R_1$ is hydroxyl and is present only when said broken line indicates a single bond;

$R_2$ is iso-propyl or sec-butyl; and $R_3$ is methoxy or hydroxy.

There are eight differnet major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below (The R group is 4'(α-L-oleandrosyl)-α-L-oleandrose):

|   | $R_1$ | $R_2$ | $R_3$ |
|---|---|---|---|
| A1a | Double Bond | sec-butyl | —OCH$_3$ |
| A1b | Double Bond | iso-propyl | —OCH$_3$ |
| A2a | —OH | sec-butyl | —OCH$_3$ |
| A2b | —OH | iso-propyl | —OCH$_3$ |
| B1a | Double Bond | sec-butyl | —OH |
| B1b | Double Bond | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The milbemycin compounds, which have a methyl or ethyl group at the 25-position and lack the 13-disaccharide group are also starting materials for the instant compounds. They are disclosed in U.S. Pat. No. 3,950,360. The antibiotic LL-F28249 compounds, which have a branched butyl, pentyl, or hexyl group containing one unsaturation at the 25-position and lack the 13-disaccharide group, are also starting materials for the instant compounds. They are disclosed in the European Patent Application No. 85106844.5.

SUMMARY OF THE INVENTION

The instant invention is concerned with certain derivatives of avermectin compounds wherein the 8,9 double bond and/or the 10,11 double bond is reduced either chemically or by catalytic hydrogenation to prepare a single bond at such positions where such single bond may optionally contain additional substituents. Thus it is an object of the instant invention to describe such reduced avermectin compounds. A further object is to describe processes for the preparation of such compounds. A still further object is to describe the uses of such compounds as anti-parasitic and insecticidal agents. Still further objects will become apparent from a reading of the following description.

DESCRIPTION OF THE INVENTION

The compounds of the instant invention have the following structural formula.

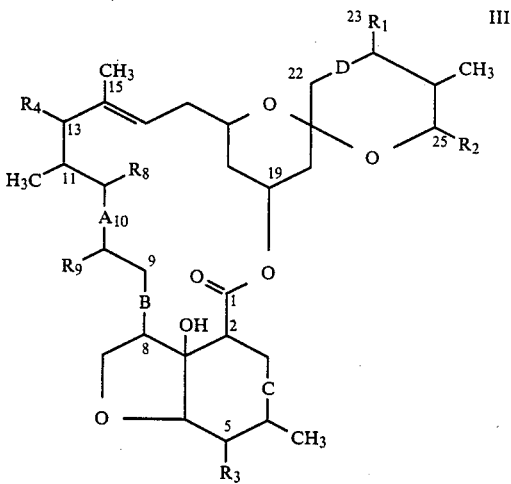

wherein A, B and C represent a single bond, double bond, or an epoxide linkage, and D represents a single bond or a double bond, provided that at all times one of A and B represents a single bond or that A and B represent single bonds and the 9,10 bond between A and B represents a double bond;

$R_1$ is hydrogen, hydroxy, or a ketone provided that $R_1$ is present only when D indicates a single bond;

$R_2$ is methyl, ethyl, iso-Propyl, sec-butyl or-$C(CH_3)=CHR_{10}$, where $R_{10}$ is methyl, ethyl, or isopropyl;

$R_3$ is hydroxy, ketone, loweralkoxy, loweralkanoyloxy or otherwise protected hydroxy;

$R_4$ is hydrogen, hydroxy, halogen, loweralkoxy, loweralkanoyloxy, $=NNHCONH_2$, $=NNHSO_2C_6H_4CH_3$, $-OCONR_6R_7$, $-NHCOAlk$, where Alk is lower alkyl, or

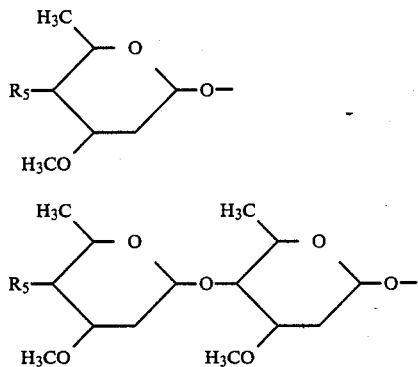

$R_5$ is hydroxy, ketone or $-NR_6R_7$;

$R_6$ and $R_7$ are independently hydrogen, loweralkyl, loweralkanoyl, loweralkylsulfonyl or substituted benzene sulfonyl, wherein the substituent is halogen;

$R_8$ is hydrogen or halogen; and $R_9$ is hydrogen, halogen, hydroxy, ketone.

In the instant description, the term "loweralkyl" is intended to include those alkyl groups containing from 1 to 6 carbon atoms in either a straight or branched chain or a cyclic configuration. Exemplary of such alkyl groups are methyl, ethyl, propyl, isopropyl, butyl, sec-butyl, pentyl, hexyl, cyclopentyl, cyclohexyl and the like.

The term "loweralkanoyl" is intended to include those alkanoyl groups of from 2 to 6 carbon atoms of either a straight or branched chain. Such groups are exemplified by acetyl, propionyl, butyryl, pentanoyl, hexanoyl and the like.

The term "halogen" is intended to include the halogen atom, fluorine, chlorine, bromine and iodine.

Preferred compounds of this invention are realized in the above structure wherein:

A is a single bond, B is a double bond or epoxide C is a double bond and D is a single bond or a double bond; $R_1$ is hydrogen or hydroxy; $R_2$ is methyl, ethyl, isopropyl, or sec-butyl; $R_3$ is hydroxy; $R_4$ is hydrogen, hydroxy, halogen, loweralkoxy, loweralkanoyloxy, 4'-$R_5$-(α-L-oleandrosyloxy), 4'-$R_5$-[4'-(α-L-oleandrosyl)-α-L-oleandrosyloxy]; $R_5$ is hydroxy, amino, loweralkylamino, diloweralkylamino $R_8$ is hydrogen, chloro or bromo; and $R_9$ is hydrogen, halogen, hydroxy or oxo.

Examples of preferred compounds of this invention are realized in the following:

10,11-dihydroavermectin B1a
10,11-dihydroavermectin B1b
10,11,22,23-tetrahydroavermectin B1a
10,11,22,23-tetrahydroavermectin B1b
10,11-dihydromilbemycin α₁
10,11-dihydromilbemycin α₃
13-deoxy-10,11,22,23-tetrahydroavermectin B1a aglycone
13-deoxy-10,11,22,23-tetrahydroavermectin B1b aglycoee
10,11-dihydroavermectin B2a
10,11-dihydroavermectin B2b
4"-amino-4"-deoxy-10,11-dihydroavermectin B1a and B1b
4"-methylamino-4"-deoxy-10,11-dihydroavermectin B1a and B1b
4"-dimethylamino-4"-deoxy-10,11-dihydroavermectin B1a and B1b
10,11-dihydro-10-hydroxyavermectin B1a and B1b
10,11-dihydro-10-fluoroavermectin B1a and B1b
10,11,22,23-tetrahydro-10-hydroxyavermectin B1a and B1b
10,11,22,23-tetrahydro-10-fluoroavermectin B1a and B1b
4"-amino-4"-deoxy-10,11-dihydro-10-fluoroavermectin B1a and B1b
4"-methylamino-4'-deoxy-10,11-dihydro-10-fluoroavermectin B1a and B1b
13-deoxy-10-fluoro-10,11,22,23-tetrahydroavermectin B1a aglycone
13-deoxy-10-fluoro-10,11,22,23-tetrahydroavermectin B1b aglycone
10,11-dihydroavermectin B1a 8,9-oxide
10,11 dihydroavermectin B1b 8,9-oxide The "b" compounds, those with a 25-iso-Propyl group, are somewhat difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound.

Alternatively, this representation of a mixture is sometimes done by referring to "the B1 or B2 compounds" or by separating the "a" compound from the "b" compound by a slash (/) such as B1a/B1b, B2a/B2b and the like.

The compounds of the instant invention differ from other avermectin compounds in that one or both of the 8,9 or 10,11 double bonds is reduced. The effect of reducing the 8,9 and/or 10,11 double bonds is that the conjugated diene system is broken. The elimination of the conjugated double bonds has a considerable effect on the ultraviolet absorption characteristics of the molecule and has resulted in a surprising and very significant increase in the stability of the molecule when it is exposed to ultraviolet light, as well as ordinary sunlight which has a significant component of ultraviolet light. This increased stability in the presence of ultraviolet light makes these compounds particularly suited to aqricultural applications and also to topical animal applications where photoinstability would be detrimental to the optimum performance of each compound.

The 8,9 and 10,11 double bonds of the avermectin starting materials are either reduced catalytically or are chemically modified. The catalytic reduction is carried out using Platinum group metals as catalysts such as platinum, palladium, rhodimm, and the like. Generally, the metal catalyst is dispersed on and supported on a substrate such as powdered carbon. The reaction is carried out under a blanket of hydrogen gas either at atmospheric pressure or pressurized up to 10 atmospheres (gauge) of hydrogen pressure in pressurable equipment ordinarily used for such reactions. The reaction is carried out in a solvent which is stable to the hydrogenation conditions and which will not adversely affect the catalyst. Lower alkanols, such as methanol, ethanol, isopropanol and the like, ethyl acetate, cyclohexane, and the like are suitable. The reaction is generally carried out at room temperature although temperature as high as 50° C. are suitable and under such conditions the reaction is complete in from 1 to 24 hours. If the hydrogenation apparatus is so equipped, the progress of the reaction may be followed by observing the amount, either in volume or in pressure drop, of hydrogen that is consumed. The products are isolated using techniques known to those skilled in the art.

The catalytic hydrogenation process generally yields a mixture of Products since the avermectin starting materials have three or four double bonds which may be hydrogenated. This would include the 3,4 and 22,23 double bonds. The 14,15 double bond is sterically hindered and generally requires more vigorous reaction conditions than are described above in order to effect hydrogenation. The various hydrogenation products are isolated from the mixture of reaction products using standard techniques such as fractional crystallization and chromatography. The double bonds which are desired to be retained in the final Product may be protected to render them inert during the hydrogenation procedure. When the hydrogenation is complete, the double bond may be regenerated by removing the protecting groups.

The 10,11 double bond may also be reacted chemically and in the process various substituents at the 10 and 11 positions ($R_9$ and $R_8$ respectively) are introduced according to the following reaction scheme where only the furan ring and carbon atoms 6 to 12 are shown in the Partial structural formulas.

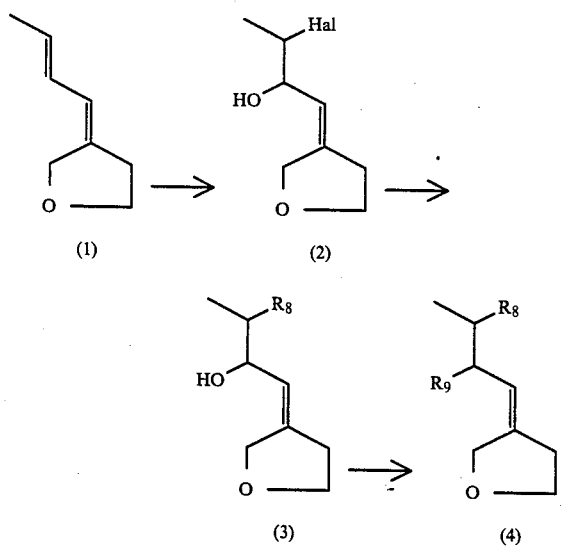

wherein $R_8$, and $R_9$ are as defined above an Hal is a halogen.

Partial structure (1) is reacted with a reagent capable of preparing a halohydrin group (a 10-hydroxy, 11-halo function). Various reagents and reaction conditions are capable of preparing a halohydrin such as N-haloacetamide, N-halosuccimide, addition of hydrochloric acid to an epoxide, and the like. Bromine is the preferred halogen. When reagents such as N-haloacetamide and N-halo succinimide are used, the reaction is carried out in an inert solvent, such as acetone, ether, tetrahydrofuran, and the like. The reaction is generally carried out at from −20° to 50° C. and is complete in from 30 minutes to 24 hours and is generally carried out in the dark.

The halohydrin compound (2) may be treated with a reducing agent, such as a trialkyltin hydride to displace the halogen with a hydrogen. Partial structures (2) and (3), with the 11-position substituent being a halogen or hydrogen constitutes the definition of $R_8$ as shown in partial structure (3). Further reactions are possible at the 10-position to convert the hydroxy group to the other groups of $R_9$ (partial structure (4)) using techniques known to those skilled in the art.

PREPARATION OF STARTING MATERIALS

The ultimate starting materials for the compounds of this invention are the avermectin fermentation products defined above which have the isopropyl or sec-butyl group at the 25-position. These compounds with a methyl or ethyl group at the 25-position and no carbohydrate function at the 13-position are often referred to as milbemycin compounds and are disclosed in U.S. Pat. No.3,950,360 to Aoki et al. Thus it is apparent that additional reactions are required to prepare many of the immediate starting materials for the instant compounds. Specifically, reactions are carried out at the 4″, 13, 22, and 23-positions. In addition, during the various reactions described above, and below it may be advisable to protect various reactive groups to prevent the undesired reaction of such groups. In addition, protection of such reaction groups may facilitate the separation of the various products. With the appropriate positions protected, the hydrogenation reaction and the other reactions may be carried out without affecting the remainder of the molecule. Following the described reactions, the protecting groups may be removed and the unprotected product isolated. The protecting groups employed is ideally one which may be readily synthesized, will not be affected by the reaction with the various reagents employed and may be readily removed without affecting any other functions of the molecule. It is noted that the instant protected compounds are novel and have considerable antiparasitic activity. They are included within the ambit of the instant invention. One preferred type of protecting group for the avermectin and milbemycin type of molecule is the tri-substituted silyl group, preferably the trialkyl silyl group. One especially preferred example, is the t-butyl dimethylsilyl group. The reaction preparing the protected compound is carried out by reacting a hydroxy compound with the appropriately substituted silylhalide, preferably the silylchloride in an aprotic polar solvent such as dimethylformamide. Imidazole is added as a catalyst. The reaction is complete in from 1 to 24 hours at from 0 to 25° C. For the 5-position hydroxy group the reaction is complete in from ½ to 3 hours at from 0° C. to room temperature. This reation is selective to the 5 position under the conditions above described and very little, if any, silylation is observed at other hydroxy substituted positions.

The silyl group are then removed after the other reactions have been carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C. Alternatively, the silyl group or groups can be removed with a hydrogen fluoride-pyridine complex in an organic solvent such as tetrahydrofuran. The reaction is complete in from about 3 to 24 hours and is preferably carried out at room temperature.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the "1"-series of compounds. Thus in the "1" series of compounds it is possible to selectively reduce the 22,23 double bond while not affecting the remaining four unsaturations or any other functional group present on the molecule. It is necessary to select a specific catalyst for the hydrogenation, one that will selectively hydrogenate the least hindered from among a series of unsaturations. The preferred catalyst for such a selective hydrogenation procedure is one having the formula:

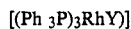

[(Ph$_3$P)$_3$RhY)]

wherein

Ph is phenyl and Y is halogen. The reduction procedure is completely described in U.S. Pat. No. 4,199,569 to Chabala et al.

Additional reactions which may be carried out to prepare the compounds of this invention are the selective removal of one of the α-L-oleandrosyl moieties (described in U.S. Pat. No. 4,206,205 to Mrozik et al.).

The reaction conditions which are generally applicable to the preparation of both the mono-saccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The Products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the mono-saccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

It has also been observed that the mono-saccharide is prepared during the course of the reaction used to remove the trialkylsilyl protecting group. Since acid catalysis is used to remove the protecting group, this is expected. However, in such cases, both the desired product and the monosaccharide are prepared and they can be readily separated using the above-described techniques.

In the preparation of the 4' or 4" keto or amino substituted compounds, the avermectin starting materials are oxidized at the 4"-position to the corresponding keto compound. The procedures for the preparation of such compounds are described in U.S. Pat. No. 4427663 to Mrozik. During the procedure the presence of any hydroxy groups at the 5 and 23-position will require that such hydroxy groups be protected in order that they too are not oxidized. The 7-hydroxy group is very unreactive and need not be protected. The procedure used to prepare the protected intermediates are described above. The oxidation reaction is carried out in an inert solvent such as methylene chloride using oxalyl chloride or trifluoroacetic anhydride in dimethylsulfoxide as the oxidizing agent. Additionally N-chlorosuccinimide in dimethylsulfide may be employed. The reaction proceeds by dissolving the oxalyl chloride or trifluoroacetic anhydride and dimethylsulfoxide (or other oxidizing reagents) in methylene chloride and cooling to from −50° to −80° C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4' or 4"-keto compound is isolated using techniques known to those skilled in the art.

In the next step, the 4' or 4"-keto compound is aminated to prepare the unsubstituted amino compound (R$_6$=R$_7$=hydrogen). The reaction is carried out in an inert solvent such as methanol at from −10° to +25° C. using ammonium salts and sodium cyanoborohydride as the aminating and reducing reagents, respectively. The reaction is complete in from 15 minutes to 24 hours and the product 4"-deoxy-4"-amino compound is isolated using techniques known to those skilled in the art. Suitable ammonium salts are the acetate, propionate, benzoate and the like. The acetate is preferred.

As a variation to the foregoing amination reaction, methyl ammonium salts can be used in place of the ammonium salts to prepare the monomethyl substituted compound directly. The same reagents, salts and reaction conditions as described above can be used for such a reaction.

The substitution reaction wherein the substituent is an acyl function is carried out using an acylating reagent in the presence of a base in an inert solvent. The acylation of avermectin compounds, is fully described in U.S. Pat. No. 4201861 to Mrozik et al. The preferred acylating reagents are loweralkanoyl anhydrides, lower alkanoyl halides, substituted benzene sulfonyl chlorides, lower alkyl sulfonyl chlorides, and the like. The reaction is carried out in an inert solvent such as methylene chloride in the presence of a non-reactive base such as pyridine or triethylamine in order to neutralize the acid produced during the course of the reaction. The reaction temperature is from $-10°$ to $25°$ C. and the reaction is complete in from 5 minutes to 8 hours. The product is isolated using known techniques.

The reaction for the preparation of the 4' or 4''-deoxy-4'- or 4''-dialkylamino compounds is carried out using the alkylating reaction conditions of an excess of a carbonyl compound, preferably formaldehyde and a reducing agent such as sodium cyano borohydride, in methanol. The reaction is carried out in a solvent suitable to dissolve the organic starting material using excess aqueous formaldehyde along with the presence of a small amount of acid such as acetic acid to facilitate the reaction. The reaction is carried out at from $-10°$ to $+25°$ C. with the solution of the avermectin compound in methanol added dropwise over a period of from 30 to 60 minutes to the alkylating reagent mixture and the product is isolated using known techniques.

Further reactions of the avermectin compounds either before or after the reduction reaction are possible to prepare the compounds of this invention. The double bonds at 3,4; 8,9; and 10,11 may be converted to epoxides using the procedures described in U.S. Pat. No. 4530921 to Mrozik. The procedures described in said reference are specifically directed to the 8,9 and 14,15 double bonds. However, they are equally applicable to the other double bonds identified above. The reaction is carried out with a mild oxidizing agent such as m-chloroperbenzoic acid, t-butyl hydroperoxide, catalyzed with vanadyl acetylacetonates, and the like. Where more than one double bond is epoxidized, the various products are readily separated using fractional crystallization and chromatographic techniques.

Following the preparation of the aglycone ($R_4$ is hydroxy at the 13 position), U.S. Pat. Nos. Re 32006 and Re 32034 to Chabala et al. disclose the hydroxy group displacement with a halogen using a reagent such as benzene sulfonylhalide, and the halogen is removed by reduction using a reducing agent such as trialkyltin hydride.

Further, rather than replace the 13-hydroxy with a halogen or hydrogen, the hydroxy can be reacted to prepare ketone, amino, imino semi-carbazide, and other 13-position ($R_4$) groups as are described in U.S. Pat. No. 4579864 to Linn et al.

The various hydroxy groups, such as at 5, 13, 23, 4' and 4'' may be alkylated following the procedures described in U.S. Pat. No. 4200581 to Fisher et al. The preparation of 13-(alkoxy)methoxy avermectin aglycone derivatives is described in U.S. Pat. No. 4,587,247.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma. Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia. Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp., and of agricultural plants such as two-spotted spider mites, (Tetranvchus so.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite add the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant processes, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed demonstrate the purity of the compounds.

In the following examples, the various starting materials therefor are avermectin compounds or derivatives of avermectin compounds. The avermectin compounds and the preparation and isolation thereof from fermentation broths are described in U.S. Pat. No. 4,310,519 issued 12 January 1982. The selective 22,23-dihydro derivatives of avermectin compounds are described in U.S. Pat. No. 4,199,569. The aglycone and monosaccharide derivatives of avermectin compounds are described in U.S. Pat. No. 4,206,205. The 13-deoxy compounds are described in U.S. Pat. Nos. Re 32006a and Re 32034. The milbemycin compounds are described in U.S. Pat. No. 3,950,360. The 4' and 4" amino compounds are described in U.S. Pat. No. 4,427,663. The acyl derivatives are disclosed in U.S. Pat. No. 4201861. The epoxide derivatives are disclosed in U.S. Pat. No. 4,530,971. The 13-keto and amino compounds are disclosed in U.S. Pat. No. 4,579,864, and the o-alkyl compounds are disclosed in U.S. Pat. No. 4,200,581. The 13-(alkoxy)methoxy compounds are disclosed in U.S. Pat. No. 4,587,247. The following examples are being provided in order that the invention may be more fully understood. They are not to be construed as being limitative of the invention.

EXAMPLE 1

5-O-t-Butyldiphenylsilylavermectin-B1a/B1b

A solution of 7.25 g of avermectin B1a/B1b in 60 mL of N,N-dimethylformamide was stirred with 3 mL of t-butyldiphenylsilyl chloride, 1.5 g imidazole, and 100 mg N,N-dimethylaminopyridine at room temperature for 48 hours. The reaction was stopped by addition of water and extraction with dichloromethane afforded the product as an oil. High performance liquid chromatography (HPLC) on silica gel using 842 1.4:3 (v:v) ethylacetate: hexane provided 7.7 g purified 5-O-t-butyl-diphenylsilylavermectin-B1a/B1b as a foam, characterized by its $^1$H NMR spectrum.

EXAMPLE 2

5-O-tert-Butyldiphenylsilyl-10,11,22,23-tetrahydro avermectin B1a/B1b.

A solution of 1.1 g 5-O-tert-butyldiphenylsilyl avermectin B1a/B1b in 10 mL of absolute ethanol and 0.2 g of 5% palladium on carbon was shaken in a Parr hydrogenator with hydrogen at 90 pounds pressure at room temperature until the drop in pressure indicated the uptake of one molar equivalent. The hydrogenation was stopped and a small sample was withdrawn for analysis. High performance liquid chromatographic analysis on a reverse phase $C_{18}$ column with a methanol-water liquid phase indicated the major components to be the 5-O-tert-butyldiphenylsilyl-22, 23-dihydroavermectin-B1a/B1b. The Parr hydrogenator was charged with another 0.2 g 5% Pd/C and the system repressurized to 84 lbs with hydrogen. After another pressure drop indicated the uptake of another molar equivalent of hydrogen, the catalyst was removed by filtration. Evaporation of the filtrate afforded a mixture of which the title compound is a major component. HPLC purification with a preparative reverse phase C18 column using a methanol-water liquid phase affords 5-O-tert-butyl-diphenylsilyl-10,11,22,23-tetrahydro avermectin B1a/B1b as an amorphous solid characterized by its $^1$H NMR and mass spectrum.

EXAMPLE 3

10,11,22,23-Tetrahydroavermectin B1a/B1b

A solution of 25 mg of 5-0-tert-butyldiphenylsilylavermectin B1a/B1b in 1 mL of tetrahydrofuran was desilylated using 3 mL of an anhydrous hydrogen fluoride-pyridine in THF solution which was prepared from 14 mL of THF, 4 ml of pyridine, and 2 ml of a commercial hydrogen fluoride-pyridine solution (consisting of ~70% HF and ~30% pyridine, supPlied by Aldrich Chemical Company) at room temperature for 20 hours under nitrogen. The reaction was worked up by addition of water followed by neutralization with sodium bicarbonate solution and extraction with ether. The ether extracts were combined and evaporated to yield a residue which was charged onto two 500 micron preparative silica gel plates. Elution with a hexane-ethyl acetate solvent afforded 10,11,22,23-tetrahydroavermectin B1a/B1b as an amorphous solid which was characterized by its 1H NMR and mass spectrum (molecular ion 876).

EXAMPLE 4

10,11,22,23-Tetrahydroavermectin B1a/B1b and 3,4,10,11,22,23-Hexahydroavermectin B1a/B1b A solution of 10.0 g of 22,23-dihydroavermectin $B_1$ (containing approximately 90% of 22,23-dihydroavermectin B1a and 9% of the lower homolog B1b) in 100 ml of absolute ethanol was shaken in the presence of 2.5 g of 5% palladium on charcoal catalyst under an atmosphere of hydrogen at 89 pounds of pressure at room temperature for one hour, when the drop in hydrogen pressure indicated the uptake of one molar equivalent. The hydrogenation was stopped, the catalyst removed by filtration, and the filtrate was concentrated to give 9.9 g of a white foam. High performance liquid chromatography on a reverse phase $C_{18}$ column with a $CH_3CN-MeOH-H_2O$ liquid phase suggested a composition of the crude reaction product of 23% 22,23-dihydroavermectin B1a/B1b, 46% 10,11,22,23-tetrahydroavermectin B1a/B1b and several other unidentified compounds. 8.7 Grams of the crude product were further purified on a silica gel column with a hexane-acetone system as solvent to give 3.8 g enriched in the desired 10,11,22,23 tetrahydroavermectin B1. The final purifcation was achieved with an aliquot of 500 mg via preparative reverse phase high performance liquid chromatography with a $MeOH-H_2O$ liquid phase which gave 280 mg of 10,11,22,23-tetrahydroavermectin B1a as a white amorphous solid after lyophilization from a benzene solution. It was characterized by its $^1$H NMR and its mass spectrum, which has a molecular ion for the mass of 876, and its UV spectrum which lacks the absorption at 245 nm. Further fractionations as described above yield 10,11,22,23tetrahydroavermectin B1b, 3,4,10,11,22,23-hexahydroavermectins B1a and B1b. The mass spectrum for 10, 11, 22, 23-tetrahydroavermectin B1a revealed major peaks at 876 (M+) and 588 (tetrahydroaglycone). The nuclear magnetic resonance spectrum of the compound (400 MHz in CDCl$_3$ with TMS as an internal standard) revealed the following major peaks: 4.3ppm (t, 1H, J=6Hz) for C$_5$—H; 4555 ppm (tq, 2H, J=2, 17Hz) for 8a-H$_2$; 4.73ppm (d, 1H, J=3Hz) for 1-H; 5.01ppm (brd, 1H, J=10Hz) for C$_{15}$—H; 5.14ppm (S, 1H) for 7—OH; 5.32 ppm (dd,1H) for C$_9$—H; 5.34 ppm (S, 1H) for C$_3$—H; 5.4 ppm (m, 1H) for C$_{19}$5.4 ppm (d,1H, J=3 Hz) for 1″ H.

EXAMPLE 5 10,11-Dihydroavermectin B2a/B2b and 3,4,10,11 tetrahydroavermectin B2a/B2b A solution of 870 mg avermectin B2a/B2b in 25 mL of absolute ethanol and 100 mg of 5% Pd/C was stirred at room temperature under one atmosphere pressure of hydrogen. After an uptake of 1.5 molar equivalent of hydrogen, the catalyst was removed by filtration. HPLC analysis using a reverse Phase C$_{18}$ column and a methanol-water liquid system indicated the composition of the mixture to be 20% avermectin B2a/B2b, 50% 10,11-dihydroavermectin B2a/B2b, 30% 3,4-dihydroavermectin B2a/B2b, and 10% 3,4,10,11-tetrahydroavermectin B2a/B2b. Preparative HPLC using a reverse Phase C$_{18}$ column and a methanol-water system followed the separation and characterization of each of the titled compounds via their 1H NMR and mass spectra.

EXAMPLE 6

13-Deoxy-10,11,22,23-tetrahydroavermectin B1a/B1 b aglycone and
13-deoxy-8,11,22,23-tetrahydroavermectin B1a/B1b aglycone A solution containing 500 mg of 13-deoxy22,23-dihydroavermectin B1a/B1b aglycone in 7.6 ml of ethanol was stirred with 176 mg of a 5% palladium on charcoal catalyst under an atmosphere of hydrogen at room temperature at slightly elevated pressure. The course of the reaction was followed by withdrawing aliquots for HPLC analysis. After 45 minutes the hydrogen atmosphere was replaced by nitrogen, the reaction mixture was filtered and the filtrate was evaporated under reduced pressure, giving 492 mg of light foam. The crude hydrogenation products were separated via high performance liquid chromatography on a Whatman Partisil M 20 10/50 ODS-3 reverse phase column employing a 52.8% CH$_3$CN-35.2% MeOH-12.0% H$_2$O-solvent mixture. The fractions were identified by analytical HPLC and TLC methods. Two pure components were isolated and identified by $^1$H-, $^{13}$C- NMR, and mass spectra as 141 mg of 13-deoxy-10,11,22,23-tetrahydroavermectin B1a aglycone and 86 mg of 13-deoxy-8,11,22,23-tetrahydroavermectin B1a aglycone in form of a white amorphous foam. Small amounts of 13-deoxy-10,11,22,23-tetrahydroavermectin B1b and 13-deoxy-8,11,22,23-tetrahydroavermectin B1a aglycones also can be obtained from the hydrogenation mixture by further careful fractionations.

EXAMPLE 7

10,11-Dihydromilbemyins $\alpha_1$ and $\alpha_3$ and 8,11-dihydromilbemycins $\alpha_1$ and $\alpha_3$.

Milbemycins $\alpha_1$ or $\alpha_3$ are reacted under the conditions of experiment 6 to give 10,11-dihydromilbemycins $\alpha 1$ and $\alpha 3$ and 8,11-dihydromilbemycins $\alpha_1$ and $\alpha_3$.

EXAMPLE 8

5-O-t-Butyldimethylsilyl-10,11,22,23-tetrahydroavermectin B1a/B1b aglycone.

A solution containing 1.0 gram of 5-O-t-butyldimethylsilyl-22,23-dihydroavermectin B1a/B1b aglycone in 15 ml of ethanol is stirred in the Presence of 300 mg of a 5% palladium on charcoal catalyst and worked up as described in experiment 6 to give 5-O-t-butyldimethylsilyl-10,11,22,23-tetrahydroavermectin B1a/B1b aglycone as an amorphous, light foam identified by $^1$H-, $^{13}$C-NMR, and mass spectra.

EXAMPLE 9

5-O-tert-Butyldiphenylsilyl-4″-oxo-10,11,22,23-tetrahydroavermectin B1a/B1b .

A solution of 1.8 g of 5-O-tert-butyldiphenylsilyl-10,11,22,23-tetrahydroavermectin B1a/B1b (prepared in Example 2) in 6 mL of dichloromethane 5 was added dropwise to a −78° C. solution of Swern reagent (250 μL DMSO and 190 μL oxalylchloride) in 6 mL of dichloromethane. After 1 hour at −78° C., 1.1 mL of triethylamine is added and the mixture was stirred another hour at −78° C. A saturated aqueous solution of ammonium chloride is added and extraction with dichloromethane afforded 1.85 g of product as a yellow foam. Purification via silica gel column chromatography using a hexane-ethyl acetate solvent system affords 1.8 g of 5-O-tert-butyldiphenylsilyl-4″-oxo-10,11,22,23-tetrahydroavermectin B1a/B1b as an amorphous solid characterized bits 1H NMR and mass spectrum.

EXAMPLE 10

4″-Amino-5-O-tert-butyldiphenylsilyl-4″-deoxy-10,11,22,23-tetrahydroavermectin B1a/B1b .

To 300 mg of the ketone from Example 9 was added 500 mg ammonium acetate, 500 mg powdered 3A molecular sieves, and 5 mL of methanol. To this stirred mixture was added a solution of 50 mg sodium cyanoborohydride in 1 mL of methanol. After 1 hour, the mixture was filtered and the filtrate evaporated. The residue was taken up in ether and wsshed with sodium bicarbonate solution. The ether was removed in vacuo and the residue purified by silica gel chromatography on four 1000 micron thick preparative plates eluted in 10% methanol-dichloromethane to afford 4″-amino-5-O-tert-butyldiphenylsilyl-4″-deoxy-10,11,22,23-tetrahydroavermectin B1a/B1b (71 mg) as an amorphous solid characterized by 1H NMR.

EXAMPLE 11

4″-Amino-4″-deoxy-10,11,22,23-tetrahydroavermectin B1a/B1b

Desilylation of 60 mg of the compound of Example 10 following the procedure established by Example 3 furnished 22 mg of 4″-amino-4″-deoxy-10,11,22,23-tetrahydro avermectin B1a/B1b as an amorphous solid characterized by its 1H NMR (200MHz, CDCl$_3$ TMS) 3.08 ppm (br S, 1H) for C-4″H and mass spectrum for 4''-epiamino-4''-deoxy-10,11,22,23, tetrahydroavermectin B$_{1a}$, C$_{48}$H$_{77}$O$_{13}$N, calculated 875.5395, found 875.5396.

EXAMPLE 12

10,11-Dihydroavermectin A2a/A2b aglycone

Avermectin A2/A2b aglycone is reacted under the conditions of experiment 6 to give 10,11-dihydroavermectin A2a/A2b aglycone.

EXAMPLE 13

10,11,22,23-Tetrahydroavermectin B1a/B1b aglycone

Avermectin B1a/B1b aglycone is subjected to the catalytic hydrogenation conditions detailed in example 6 to give 10,11,22,23-tetrahydroavermectin B1a/B1b aglycone.

EXAMPLE 14

10,11-Dihydro-11-bromo-10-hydroxyavermectin B1a/B1b

To 380 mg avermectin B1a/B1b in 9 mL of acetone and 1 mL of water was added 100 mg of N-bromoacetamide. The mixture was stirred in the dark at room temperature for 1 hour and work up consists of addition of water and extraction with dichloromethane. The solvent was removed in vacuo and the residual solid purified by preparative thick layer silica gel chromatography using a ethylacetate-hexane solvent system to afford 80 mg of 10,11-dihydro-11-bromo-10-hydroxyavermectin B1a/B1b as an amorphous solid characterized by its 1H NMR spectrum.

EXAMPLE 15

10,11-Dihydro-11-bromo-10-hydroxy-4'',5di-O-t-butyl-dimethylsilyl avermectin B1a/B1b The procedure set forth for Example 14 was followed using 6.0 g of 4'', 5-di-O-tert-butyl-dimethylsilylavermectin B1a/B1b as the starting material. The product (4.0 g) was an amorphous solid characterized by its 1H NMR spectrum.

EXAMPLE 16

10,11-Dihydro-10-hydroxyavermectin B1a/B1b

A solution of 80 mg of 10,11-dihydro-11-bromo-10-hydroxyavermectin B1a/B1b and 300 μL of tri-n-butyl-tin hydride in 5 mL of toluene was heated at 100° C. under nitrogen for 2 hours. Column chromatography on silica gel using hexane-ethylacetate provided an initial separation of the product from the tin compounds. Final purification of the title compound was achieved by HPLC on a C$_{18}$ reverse phase column using a methanol-water liquid phase. Structural confirmation is by 1H NMR and mass spectrum for 10,11-dihydro-10-hydroxyavermectin B1a/B1b. The mass spectrum for 10,11-dihydro-10-hydroxyavermectin B1a/B1b calculated for C$_{41}$H$_{60}$O$_{11}$: (M+ less sugar, less water) calculated: 728.4136; found 728.4138. The nuclear magnetic resonance spectrum for the product (400 MHz in CDCl$_3$, TMS) revealed the following major peaks=4.30 ppm (br t, J=8 Hz) for C$_5$—H; 4.40 ppm (br S) for C$_{10}$H; 4.74 ppm (d, J=3 Hz) C$_1$—H; 4.80 ppm (tq, J=3, 15 Hz) for 8a-H; 4.99 ppm (d J=10 HZ) for C15H; 5.25 ppm (S) for C7—OH; 5.31 ppm (sq, J=2Hz) for C$_3$-H; 5.33 ppm (q, J=3H) for C$_9$—H; 5.40 ppm (d, J=4 Hz) for C—1''—H; 5.44 ppm (m) for C$_{19}$—H; 5.59 ppm (dd, J=3,10 Hz) for C$_{22}$—H; and 5.79 ppm (dd, J=2,10 Hz) for C$_{23}$-H.

EXAMPLE 17 0,11-Dihydro-10-hydroxy-4'', 5-di-O-tert-butyldimethylsilyl avermectin B1a/B1b The title compound was obtained from the bromohydrin of Example 15 following the tin hydride reduction procedure outlined in Example 16. The product as purified by HPLC was an amorphous solid characterized by its 1H NMR and mass spectrum as 10,11-dihydro-10-hydroxy-4'', 5-di-O-tert-butyldimethyllsilylavermectin B1a/B1b.

EXAMPLE 18

10,11-Dihydro-10-oxo-4'', 5-di-O-tert-butyldimethylsilyl avermectin B1a/B1b

Starting with the compound from Example 17 following the Swern oxidation procedure established by Example 9, the 10-hydroxy function was oxidized to a ketone obtained as an amorphous solid characterized by its 1H-NMR spectrum as 10,11-dihydro-10-oxo-4'', 5-di-O-tert-butyldimethylsilyl avermectin B1a/B1b.

EXAMPLE 19

10, 11-Dihydro-10-oxo-avermectin B1a/B1b

The compound from Example 18 was desilylated with hydrogen fluoride-pyridine following the procedure of Example 3 to provide an amorphous solid characterized by its 1H NMR and mass spectrum as 10,11-dihydro-10-oxo-avermectin B1a/B1. The mass spectrum for 10,11-dihydro-10-oxoavermectin B1a was calculated at 852.4660 and found as 852.4656 (for M+ $^{less\ two\ water}$). The nuclear magnetic resonance spectrum'$^s$ (200 MHz, CDCl$_3$, TMS) major peaks are as follows: 4.74 ppm (d, J=3Hz) for Cl'—H; 4.98 ppm (M) for C8a—H; 5.02 ppm (br d) for C$_{15}$—H; 5.32 ppm (S) for C$_3$—H; 5.40 ppm (d, J=3Hz) for C$_1$''H; 5.50 ppm (M) for C$_{19}$—H; 5.58 ppm (dd, J=3,10 Hz C$_{22}$—H; 5.80 ppm (dd, J=2,10Hz) for C$_{23}$H; and 6.15 ppm (S) for C$_9$—H.

EXAMPLE 20

10,11Dihydro-10-fluoro-4'', 5-di-O-tert-butyl=dimethylsilyl avermectin B1a/B1b A solution of 100 mg of 10,11-dihydro-10-hydroxy-4'', 5-di-O-tert-butyldimethylsilyl avermectin B1a/B1b in 3 mL of hexane at −78° C. was stirred with 100 μL of diethylaminosulfur trifluoride (DAST) under nitrogen. After 1.5 hours, the reaction was quenched with a 7% aqueous sodium carbonate solution and the product extracted with dichloromethane. Purification by preparative thick layer silica gel chromatography using an ethyl acetate hexane solvent system afforded 45 mg of 10,11-dihydro-10-fluoro 4'',5-di-O-tert-butyldimethylsilyl avermectin B1a/B1b as an amorphous solid characterized by its 1H-NMR.

EXAMPLE 21

10,11-Dihydro-10-chloro 4'', 5-di-O-tert-butyl=dimethylsilyl avermectin B1a/B1b To 400 mg of 10,11-dihydro-10-hydroxy-4'', 5-di-O-tert-butyldimethylsilyl avermectin B1a/B1b in 1.0 mL of THF at 0° C. was added 150 μL of hexachloroacetone followed by 300 mg of triphenylphosphine dissolved in 1 mL of THF. After 1.5 hours at 0° C., the solvent was removed in vacuo and the residual solid fractionated on preparative thick layer silica gel using a hexane-ethyl acetate solvent system to afford 120 mg of 10,11-dihydro-10-chloro 4″, 5-di-O-tertbutyl=dimethylsilyl avermectin B1a/B1b as an orange amorphous solid characterized by its 1H-NMR spectrum.

EXAMPLE 22

10,11-Dihydro-10-fluoroavermectin B1a/B1b.

The compound from Example 20 was desilylated with hydrogen fluoride-pyridine according to the procedure outlined by Example 3. After fractionation on preparative thick layer silica gel plates, the compound was purified by HPLC on a $C_{18}$ reverse phase column using a methanol-$H_2O$ system to afford an amorphous solid characterized by its 1H NMR and mass spectrum as 10,11-dihydro-10-fluoro-avermectin B1a/B1b. The mass spectrum for 10,11-dihydro-10-fluoroavermectin B1a was found at 730.4091 (M+ less sugar, less water). The nuclear magnetic resonance spectrum's (300 MHz, $CDCl_3$ TMS) major peaks are as follows: 4.70 ppm (M) for $C_{1'}$—H, C8a—H; 4.80 ppm (br m) for $C_9$—H; 4.94 ppm (S) for $C_7$-OH; 5.04 ppm (d) for $C_{15}$—H; 5.31 ppm (S) for $C_3$-H; 5.40 ppm (d) for $C_{1''}$—H; 5.45 ppm (M) for $C_{19}$—H; 5.57 ppm (dd, J=3, 10Hz) for $C_{22}$-H; 5.78 ppm (dd, J=2,10Hz) for $C_{23}$6—H.

EXAMPLE 23

10,11-Dihydro-4″,5-di-O-t-butyldimethylsilylavermectin B1a/B1b

To a solution of 500 mg (0.45 mmol) of 4″-5-di-O-t-butyldimethylsilyl-10-hydroxyavermectin-B1a/B1b in 10 mL of dry dichloromethane was added 0.5 mL of freshly distilled triethylamine. The mixture was cooled to 0° C. and 500 mg (1.5 mmole) of dichlorotriphenylphosphorane was added in one portion. After 30 minutes, the cooling bath was removed and the mixture was stirred an additional 1.5 hours at room temperature. The mixture was then transferred directly to a 5.5×40 cm glass column containing 75 g of silica gel and eluted with 2 column volumes of 20% ethyl acetate: hexane. Evaporation of the solvent fraction afforded 460 mg of a yellow glass. This mixture of chlorides (8-chloro-8,11-dihydro- and 10-chloro-10,11-dihydro-4″-5-O-t-butyldimethylsilylavermectin B1a/B1) was reduced in 3 mL of toluene with 3 mL of tri-n-butyltin hydride at 110° C. for 12 hours to afford, after flash silica gel chromatography, 306 mg of product. 1H NMR analysis indicated a 2:1 mixture of the 10,11-dihydro and 8,11-dihydro-4″, 5-di-O-t-butyldimethylsilyl-avermectin B1a/B1b. These two isomers were separated by reverse phase HPLC using a methanol-water solvent system and individually characterized by their 1H NMR and mass spectra.

EXAMPLE 24

5-O-Tert-butyldimethylsilyl-11-bromo-10,11-dihydro-10, 13-dihydroxy-milbemycins $\alpha_1$ and $\alpha_3$ (also called A3 and A4).

A solution of 1.25 g of 5-O-tert-butyl-dimethylsilyl-13-hydroxymilbemycins $\alpha_1$ and/or $\alpha_3$ (obtained according the procedure described in EUROPAISCHE PATENTANMELDUNG, Veroffentlichungsnummer 0 186 043, Beispiel 1.17) in 30 ml of acetone and 3 ml of water is reacted with 365 mg of N-bromoacetamide according to the procedure detailed in example 34 to give 5-O-tert-butyldimethylsilyl-11-bromo-10,11-dihydro-10,13-dihydroxy-milbemycins $\alpha_1$ and $\alpha_3$, *which are identified by* 1H, 13C-NMR and mass spectra.

EXAMPLE 25

5-O-Tert-butyldimethylsilyl-10,11-dihydro-10,13dihydroxymilbemycins $\alpha_1$ and $\alpha_3$ (also called A3 and A4)

A solution of the crude reaction product obtained in the reaction described in example 24 containing 5-O-tert-butyldimethylsilyl-11-bromo-10,11-dihydro-10,13-dihydroxymilbemycins $\alpha_1$ and $\alpha_3$ as the major components, 100 mg of 2,2′-azobis(2-methylpropionitrile), and 3.0 ml of tri-n-butyltin hydride in 25 ml of toluene is stirred under $N_2$ in an oil bath heated to 85° C. as described in detail in example 35. Isolation and purification of the major reaction products according to the procedure of example 35 gives 5-O-tert-butyldimethylsilyl-10,11-dihydro-10,13-dihydroxymilbemycins $\alpha_1$ and $\alpha_3$, which are identified by 1H, 13C-NMR and mass spectra.

EXAMPLE 26

5-O-Tert-butyldimethylsilyl-10,11-dihydro-10-fluoroavermectin B1a/B1b aglycone.

A solution of 1.0 g of 10,11-dihydro-10-fluoroavermectin B1a/B1b aglycone (from Example 32) in 20 ml of DMF is stirred at room temperature under $N_2$. Sequentially 0.6 g of imidazole followed by 0.75 g of t-butyldimethylsilyl chloride are added. After 40 minutes the reaction mixture is poured onto 150 ml of water and extracted with $CH_2Cl_2$. The extract is washed with water, dried and concentrated in vacuo to a thick oil. This is purified by chromatography on a column of 30 g of silica gel with $CH_2Cl_2$-EtOAc solvent mixture to give 5O-tert-butyldimethylsilyl-10,11-dihydro-10-fluoroavermectin B1a/B1b aglycone, which is identified by mass and NMR spectra.

EXAMPLE 27

5-O-Tert-butyldimethylsilyl-13-chloro-10,11-dihydro-10-fluoroavermectin B1a/B1b aglycone A solution of 500 mg of 5-O-tert-butyldimethylsilyl-10,11-dihydro-10-fluoroavermectin B1a/B1b aglycone, 0.75 ml (600 mg) of N,N-diisopropylethylamine, and 750 mg of 4-dimethylaminopyridine is stirred at room temperature under $N_2$. To this a solution of 800 mg of 2-nitrobenzenesulfonyl chloride in 10 ml of $CH_2Cl_2$ is added dropwise during 10 minutes and the reaction mixture is stirred at room temperature for two hours. It is then poured onto 200 ml of water and extracted with ether. The extract is washed with water, dried and concentrated in vacuo to a light foam. Purification on several 1000 micron thick silica gel layer chromatography plates gave pure 5O-tert-butyldimethylsilyl-13-chloro-10,11-dihydro-10-fluoroavermectin B1a/B1b aglycone, which is identified by mass and NMR spectra.

EXAMPLE 28

5O-Tert-butyldimethylsilyl-13-deoxy-10,11-dihydro-10fluoroavermectin B1a/B1b aglycone A solution of 260 mg of 5-O-tert-butyldimethylsilyl-13-chloro-10,11-dihydro-10-fluoroavermectin B1a/B1b aglycone and 35 mg of 2,2′-azobis(2-methylpropionitrile) in 5 ml of dry toluene is stirred in an oil bath maintained at 80° to 85° C. and kept under a blanket of nitrogen. Through a syringe 1.0 ml of tri-n-butyltin hydride are added rapidly and the course of the reaction is followed by analyses of probes on a reverse phase HPLC column. After 4 hours reaction time the mixture is concentrated in high vacuo to a residue of about 2 ml. This is diluted with $CH_2Cl_2$ and purified in a column containing 15 g of silica gel. The solvent is changed to $CH_2Cl_2$-EtOAC (9:1), and the product is collected and identified by its mass and $^1H$ NMR spectra as 5-O-tert-butyldimethylsilyl-13-deoxy-10,11-dihydro-10-fluoroavermectin B1a/B1b aglycone.

EXAMPLE 29

13-Deoxy-10,11-dihydro-10-fluoroavermectin B1a/B1b aglycone

A solution containing 167 mg of 5O-tert-butyldimethylsilyl-13-deoxy-10,11-dihydro-10-fluoroavermectin B1a/B1b aglycone and 170 mg of p-toluenesulfonic acid monohydrate in 17 ml of methanol is stirred at room temperature for 30 minutes and then immediately poured into 40 ml of an aqueous $NaHCO_3$ solution. This is extracted with 100 ml of ether and washed successively with aqueous $NaHCO_3$ solution and water, dried over $MgSO_4$, and concentrated in vacuo to a light foam. It is purified on two 1 mm thick preparative silica gel layer plates with a hexaneEtOAc (1:1) solvent mixture to give 13-deoxy-10,11-dihydro-10-fluoroavermectin B1a/B1b aglycone, which is characterized by its mass and $^1H$ NMR spectra.

EXAMPLE 30

10,11-dihydroavermectin - B1a/B1b

To a solution of 300 mg of 10,11-dihydro-4",5-di-O-t-butyldimethylsilylavermectin-$B_{1a}$/B1b in 2 mL of tetrahydrofuran in a polypropylene vessel was added 16 mL of hydrogen fluoride-pyridine in tetrahydrofuran (prepared by diluting 15 ml of commercially available 70% HF-pyridine with 35 mL dry pyridine and 60 ml of tetrahydrofuran). The reaction mixture was stirred for 3 days at 20° C. under a dry nitrogen atmosphere. The mixture was then quenched with water, neutralized with sodium bicarbonate, and the organic product was extracted with ether. The ether extracts were combined, dried (anhydrous magnesium sulfate), and evaporated in vacuo to yield 200 mg of products of which the title compound was the major component. Subsequent HPLC purification on a Whatman Partisil M20 10/50 ODS-3 reverse phase column employing a 85:15 methanol-water solvent system afforded 86 mg of 10,11-didyroavermectin B1a/B1b as a white amorphous solid, identified by its $^1H$ and $^{13}C$-NMR and mass spectra.

EXAMPLE 31

10,11-Dihydroantibiotic LL-F28249 β

A solution of 500 mg of antibiotic LL-F28249 β (obtained by fermentation of the microorganism *Streptomyces cyaneogriseus* subsp. noncyanogenus LL-F28249, NRRL No. 15773 and isolation as described in European Patent Application No. 85106844.5 Publication Number 0 170 006) is hydrogenated and purified according to the procedure described in Example 6 to give 10,11-dihydroantibiotic LL-F28249 β, which is identified on hand of its $^1H$, $^{13}C$-NMR and mass spectra.

EXAMPLE 32

10,11-Dihydro-10-fluoroavermectin B1a/B1b mono-saccharide and
10,11-dihydro-10-fluoroavermectin B1a/B1b aglycone A mixture of 4.6 ml of water, 4.6 ml of concentrated $H_2SO_4$ and 17 ml of tetrahydrofuran is added slowly to a solution of 2.2 g of 10,11-dihydro-10-fluoro-4", 5-di-O-tert-butyldimethylsilyl avermectin B1a/B1b (obtained in example 20) and left at room temperature for 24 hours under an atmosphere of nitrogen. Then the dark reaction mixture is poured onto 100 ml of a ice-water mixture, extracted with $CH_2Cl_2$ and washed with aqueous dilute sodium bicarbonate solution and water. The $CH_2Cl_2$ solution is dried over $MgSO_4$ and concentrated under vacuo to a dark foam. Chromatgraphy of the crude reaction product on a column of silica gel with a $CH_2Cl_2$-EtOAc solvent mixture affords pure 10,11-dihydro-10-fluoroavermectin B1a/B1b aglycone and 10,11-dihydro-10-fluoroavermectin B1a/B1b monosaccharide, which are characterized by their mass and $^1$NMR spectra.

EXAMPLE 33

8,9-Epoxy-10,11,22,23-tetrahydroavermectin-B1a/B1b

To a solution of 100 mg (0.11 mmol) of 10,11,22,23-tetrahydroavermectin B1a/B1b in 5 mL of dry dichloromethane was added 5 mg of vanadium acetylacetonate followed by 50 microliters of a 3 molar t-butylhydroperoxide in toluene solution (1.3 eq). The solution's color changed immediately from green to brown and then over 30 minutes became yellow. The mixture was stirred at 20° C. for 18 hours and the solvent was concentrated in vacuo. The concentrate was fractionatd on two 500 micron preparative silica gel plates eluted with a 2:1 ethyl acetate-hexane solvent system. The yellow band with the $R_f$ of 0.2–0.6 was extracted to afford 92 mg of a yellow foam. Further purification by reverse phase HPLC employing a 90:10 methanol-water system afforded 49 mg of the 8,9-epoxide as an amorphorous solid characterized by its $^1HNMR$ and mass spectrum.

EXAMPLE 34

11-Bromo-10-hydroxy-10,11,22,23-tetrahydroavermectin B1a/B1b

A solution of 2.0 g of ivermectin (mixture of 22,23-dihydroavermectin B1a and B1b ) in 31.2 ml of acetone and 3.12 ml of water was stirred at room temperature. In one Portion 364 mg of N-bromoacetamide was added and the reaction mixture was continued to stir for 21 hours in the dark. At that time TLC and HPLC analyses of a probe of the mixture indicated that three new products, but little starting material was present in the reaction mixture. The major component was assumed to be 11-bromo-10-hydroxy-10,11,22,23-tetrahydroavermectin B1a/B1b in analogy to example 14, and the crude reaction product was further reacted in example 35, which confirmed this structural assignment.

EXAMPLE 35

10-Hydroxy-10,11,22,23-tetrahydroavermectin $B_{1a}$/B1b

A solution of 2.0 g of crude reaction product obtained in example 34 containing 11-bromo-10-hydroxy-10,11,22,23-tetrahydroavermectin B1a/B1b as the major component and 106 mg of 2,2'-azobis(2methyl-propionitrile) in 25 ml of toluene was stirred under $N_2$ in an oil bath heated to 85° C. To this 3.1 ml of tri-n-butyltin hydride was added in one portion and heating was continued for 1.25 hours. The reaction mixture was allowed to come to room temperature and then poured onto water. The products were extracted with ether, the extract washed with water, dried, and concentrated in high vacuo to 6 g of oil. This was purified by column chromatography on 200 g of silica gel with $CH_2Cl_2$ containing from 0 to 5% of methanol as solvent. This afforded 612 mg of pure 10-hydroxy-10,11,22,23-tetrahydroavermectin B1a/B1b in form of a colorless glass, which was characterized by $^1H$, $^{13}C$-NMR and mass spectra. Further fractionations carried out on a reverse phase preparative HPLC column with some of the fractions of this silica gel column gave one Product, which is isomeric with the major product, and a second byproduct, which is the dehydration product of the latter.

EXAMPLE 36

10-Hydroxy-10,11,22,23-tetrahydroavermectin B1a/B1b aglycones

A solution of 657 mg of 10-hydroxy-10,11,22,23-tetrahydroavermectin B1a/B1b in 15 ml of methanol containing 1% of concentrated $H_2SO_4$ (by volume) was kept for 25 hours at room temperature. Then the solution was diluted with ether and washed sequentially with water, aqueous $NaHCO_3$ solution and water, dried and concentrated in vacuo to 438 mg glass. This was purified by chromatography on a reverse phase preparative HPLC column to give 275 mg of 10-hydroxy-10,11,22,23-tetrahydroavermectin B1a/B1b aglycones identified by $^1H$, $^{13}C$-NMR and mass spectra.

EXAMPLE 37

5-O-Tert-butyldimethylsilyl-10-hydroxy-10,11,22,23tetrahydroavermectin B1a/B1b aglycones A solution of 65 mg of 10-hydroxy-10,11,22,23-tetrahydroavermectin B1a/B1b aglycones and 36 mg of imidazole in 0.5 ml of DMF was stirred at room temperature. In one portion 38 mg of tert-butyldimethylsilyl chloride were added and allowed to react for 2 hours. It was then diluted with 10 ml of water and the product was extracted with EtOAc. The extract was concentrated to 88 mg of white foam. It was purified by chromatography on 1 mm thick silica gel layer plates with a $CH_2Cl_2$ EtOAc solvent mixture to give 40 mg of 5-O-tert-butyl-dimethylsilyl-10-hydroxy-10,11,22,23-tetrahydroavermectin B1a/B1b aglycones and 30 mg of recovered starting material, which both were identified by their $^1H$, $^{13}C$-NMR and mass spectra.

EXAMPLE 38

5-O-Tert-butyldimethylsilyl-10,13-difluoro-10,11,22,23-tetrahydroavermectin B1a/B1b aglycones A solution of 50 microliter of diethylaminosulfur trifluoride (DAST) in 2.0 ml of $CH_2Cl_2$ is stirred at $-78°$ C. under $N_2$. To this a solution of 250 mg of 5-O-tert-butyldimethylsilyl-10-fluoro-10,11,22,23-tetrahydroavermectin B1a/B1b aglycones Prepared from 10,11-dihydro-10-fluoro avermectin B1a/B1b aglycone (from Example 32) according to the Procedure of Example 37, is added slowly from a syringe and the mixture is kept at minus 78° for 30 minutes. Then it is poured onto an aqueous $NaHCO_3$ solution and extracted with ether. The extract is washed with water and concentrated to a light foam, which is purified by repeated preparative silica gel layer chromatographieson 1000 and 500 micron thick Plates with hexane-EtOAc solvent mixtures, and identified by $^1H$, $^{13}C$-NMR and mass spectra as 5-O-tert-butyldimethylsilyl-10,13-difluoro-10,11,22,23-tetrahydroavermectin B1a/B1b aglycones.

EXAMPLE 39

10,13-Difluoro-10,11,22,23-tetrahydroavermectin B1a/B1b aglycones

A solution of 80 mg of 5-O-tert-butyldimethylsilyl-10,13-difluoro-10,11,22,23-tetrahydroavermectin B1a/B1b aglycones in 4.0 ml of methanol containing 40 mg (1%) of p-toluenesulfonic acid monohydrate is kept at room temperature for 30 minutes and then poured onto aqueous $NaHCO_3$ solution. This is extracted with ether, the extract washed with water, dried, and concentrated in vacuo. The residue is purified on a 1000 micron thick silica gel layer preparative chromatography plate to give 10,13-difluoro-10,11,22,23-tetrahydroavermectin B1a/B1b aglycones which are identified by $^1H$, $^{13}C$-NMR and mass spectra.

EXAMPLE 40

8,9,10,11-tetrahydro-10-oxo-4'',5-di-O-t-butyldimethylsilyl-BB1b avermectin

The 5.0 mL of a commercially available 1.0 M lithium aluminum hydride in ethyl ether solution under an atmosphere of nitrogen was added 0.5 mL of anhydrous methanol. The resulting white slurry was stirred at 20° C. for 30 minutes before the solvent was removed in vacuo. Copper (I) bromide (0.36g) was then transferred into the flask containing the lithium trimethoxy aluminum hydride under a nitrogen atmosphere in a glove bag. The flask with the resulting solid mixture was sealed with a rubber septum and cooled to 0° C. Tetrahydrofuran (5.0 mL) was then added and a black precipitate was formdd. This mixture was stirred at 0° C. for 30 minutes, cooled to $-78°$ C., and 0.5 mL of dry sec-butanol was added followed by a solution of 100 mg 10-oxo-4'',5-di-o-t-butyldimethylsilyl-10,11-dihydroavermectin B1a/B1b in 2 mL of tetrahydrofuran. The resulting mixture was a black paste which required the addition of another 6 mL of tetrahydrofuran to permit stirring. The mixture was stirred at ca. $-22°$ C. (frozen carbon tetrachloride bath) for 2 hours. A saturated ammonium chloride solution was then added to quench the reaction and the product was extracted with ether. The ether extracts were combined, dried and evaporated to afford 85 mg of crude product. Purification by preparative thick layer silica gel chromatography using a 2:1 hexane: ethyl acetate solvent system afforded 50 mg of pure product. Partial $^1H$ NMR (300 MHz): 4.3 (t, 1H, J=9Hz), 4.4 (br s, 1H), 4.7 (d, 1H, J=3 Hz), 4.9 (S, 1H), 5.15 (br m, 1H), 5.3 (br s, 2H), 5.34 (m, 1H), 5.6 (dd, 1H, J=2, 9 HZ), 5.8 (dd, 1H, J=1,91 Hz); $^{13}CNMR$, 116.72, 120.18, 127.55, 135.87, 136.39, 137.19.

EXAMPLE 41

5-O-t-butyldimethylsilyl-10,11,-dihydroavermectin B1a and B1b and
5-O-t-butyldimethylsilyl-8,11-dihydroavermectin B1a and B1b 5-O-t-butyldimethylsilyl avermectin B1a/B1b (prepared according to the procedure described by Mrozik et al. in J. Med. Chem. 1982, 25, 658–663) was reacted according to the procedures described in Examples 14, 16 and 23 to give title comPounds after separation by HPLC according to techniques known by those skilled in the art. Mass sPectrum for 5-O-t-butyldimethylsilyl-10,11-dihydro avermectin B1b:974.5801: Nuclear magnetic resonance (300 MHz, $CDCl_3$, TMS) are as follows: 1.05 Ppm (d, J=7 Hz) for methyl of i-propyl, 1.09 ppm (d, J=Hz) for methyl of i-propyl, 4.45 ppm (br s) for $C_5$—H, 4.51 ppm (AB, Jab=13 Hz) for C8a-H, 4.74 ppm (d, J=4 Hz for $C_1'$—H, 5.00 ppm (d, J=7 Hz) for $C_{15}$-H, 5.23 ppm (s) for C7—OH, 5.25 ppm (dd) for $C_9$-H, 5.27 ppm (s) for C3—H, 5.40 ppm (d, J=4 Hz) for $C_1''$-H, 5.45 ppm (m) for $C_{19}$—H, 5.58 ppm (dd, J=3,10 Hz) for $C_{22}$-H, 5.75 ppm (dd, J=2, 10 Hz) for $C_{23}$-H.

8,11-dihydro-5-O-t-butyldimethylsilylavermectin-B1b Mass spectrum:974.5820: Nuclear magnetic resonance (300 MHz, CDCl$_3$, TMS) major peaks are as follows: 1.05 ppm (d, J=8 Hz) for methyl of i-propyl, 1.09 ppm (d, J=8Hz) for methyl of i-propyl, 1.95 ppm (m, J=3,6 Hz), 2.95 ppm (q, J=9 Hz), 4.10 ppm (t, J=9 Hz), 4.98 ppm (dd, J=8,13 Hz) for $C_{10}$-H, 5.80 ppm (m) for C-11-H.

EXAMPLE 42

UV-irradiation of 10,11,22,23-tetrahydroavermectin B1 and of 22,23-dihydroavermectin B1

Avermectin derivatives were irradiated in solution in a quartz vessel with UV light (maximum at 300 nm) in order to simulate their stability under exposure to sunlight when applied to agricultural crops. In all cases compounds lacking the 8,9,10,11-diene function showed extended stabilities.

A solution of 5 mg of 10,11,22,23-tetrahydroavermectin B1 in 5.0 ml of methanol in a quartz tube was irradiated for a total of 40 hours. Aliquots were removed at certain time intervals and injected directly into a reverse phase HPLC column for analysis. The compounds were detected by their UV absorption at 200 nm. The retention times and areas (in AUC units) of the peaks were recorded as a measure of the identities and quantities of the compounds remaining in the reaction mixture. At the start of the irradiation the solution showed two peaks at 10.2 and 12.1 minutes in a ratio of 20 to 80% for the "b" and the "a" homologs respectively with a combined total area of 28238. The area after 40 min, 6, 20, and 40 hours was 29465, 24530, 21206, and 10265. This corresponds to 104, 87, 75, and 36% of 10,11,22,23-tetrahydroavermectin B1 remaining.

For comparison, a solution of 5 mg of 22,23-dihydroavermectin B1 in 5.0 ml of methanol in a quartz tube was irradiated for a total of 20 hours. Aliquots were removed and analysed as described above. However, the decomposition of an avermectin containing the 8,9,10,11-diene functionality is further complicated due to the fast formation of isomers of the 8,9-, and the 10,11-double bonds. At the start of the irradiation this solution showed two peaks at 8.7 and 10.2 minutes in a ratio of 9 to 86% for the "b" and the "a" homologs respectively with a combined total area of 21045. After 40 minutes of irradiation three peaks are observed with retention times of 8.6, 10.3, and 11.6 minutes in a ratio of 15, 48, and 36%. Isolation of the three peaks in an independent experiment and resolving the 8.6 min peak into two distinct compounds by further chromatographic purification, and structure determination by mass and NMR spectra fixed the structures of the compounds of the 8.6 min Peak as 22,23-dihydroavermectin B1b and 10,11-Z-22,23-dihydroavermectin B1a, of the 10.2 min peak as the desired 22,23-dihydroavermectin B1a, and of the 11.6 min peak as 8,9-Z-22,23-dihydroavermectin B1a. Thus following the decomposition of the 22,23-dihydroavermectin B1a contained in the 10.2 min peak by the areas at the start, after 40 min, after 6 and 20 hours as 17407, 9774, 6236, and less than 1000, the remaining 22,23-dihydroavermectin B1a could be determined as 100, 56, 36, and less than 5%.

It has been shown by this experiment that after 20 and 40 hours of UV-irradiation 75 and 36% of the 10,11-dihydro derivative but less than 5% of the 8,9,10,11-diene containing avermectin respectively remained undecomposed.

EXAMPLE 43

Residual activities of Avermectin B1 and of 10,11-dihydro-10-fluoroavermectin B1 against the two spotted spider mite (*Tetranychus urticae*)

Bush bean plants, var. Tendercrop, were treated with the pesticides by a short immersion into an aqueous solution of the pesticide at the specified concentrations. The plants were separated into three groups, each group being infected with the mites 0, 8, and 15 days after treatment, respectively. After an additional four days the number of dead and live mites was determined. This experimental procedure corresponds to a standard method used for the determination of residual mite activities.

| | RESULTS: | | | |
|---|---|---|---|---|
| | Concentration | % Twospotted Spider Mite Mortality | | |
| Compound | in ppm | 4 days | 12 days | 19 days |
| AVERMECTIN B1 | 0.03 | 72 | 15 | 1 |
| | 0.1 | 96 | 51 | 20 |
| | 0.3 | 100 | 96 | 95 |
| | 1.0 | — | 100 | 100 |
| 10,11-DIHYDRO-10-FLUOROAVERMECTIN B1 | 0.03 | 93 | 45 | 11 |
| | 0.1 | 100 | 100 | 75 |
| | 0.3 | 100 | 100 | 100 |
| | 1.0 | — | 100 | 100 |
| CONTROL | 0.00 | 2 | 2 | 0 |

This experiment shows that the 10,11-dihydro compound retains a higher activity over a longer time period than the compound containing a UV light absorbing 8,9,10,11-diene in the molecule.

What is claimed is:
1. A compound having the formula:

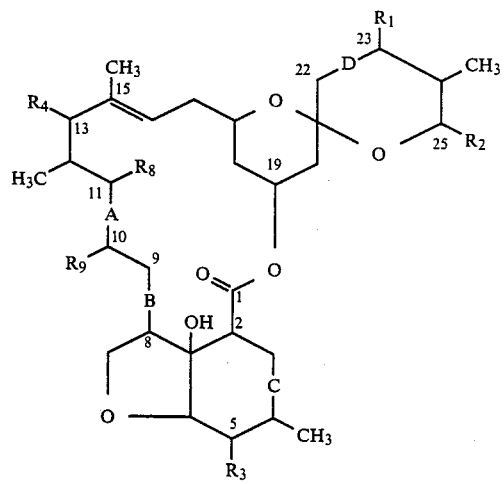

wherein A is a single bond, B and C each represent a double bond, and D represents a single bond or a double bond;

$R_1$ is hydrogen, hydroxy or a ketone provided that $R_1$ is present only when D indicates a single bond;

$R_2$ is methyl, ethyl, iso-propyl or sec-butyl or —C(CH$_3$)=CHR$_{10}$ where $R_{10}$ is methyl, ethyl or isopropyl;

$R_3$ is hydroxy, loweralkoxy, lower-alkanoyloxy or otherwise protected hydroxy or $R_3$, together with the adjacent carbon atom and the hydrogen attached thereto, form a carbonyl group;

$R_4$ is hydrogen, hydroxy, halogen, loweralkoxy, loweralkanoyloxy,

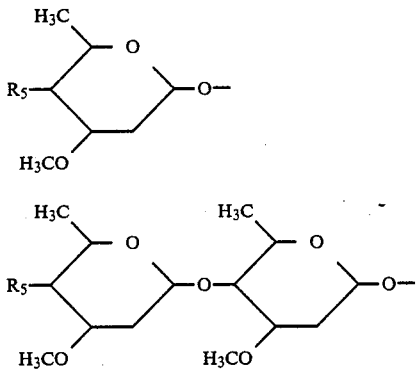

$R_5$ is hydroxy, or —NR$_6$R$_7$ or $R_5$, together with the adjacent carbon atom and the hydrogen attached thereto, form a carbonyl group;

$R_6$ and $R_7$ are independently hydrogen, loweralkyl, or lowerlkanoyl;

$R_8$ is hydrogen or bromo;

$R_9$ is hydrogen, halogen, hydroxy, or $R_9$ together with the adjacent carbon atom and the hydrogen attached thereto, form a carbonyl group; and the 4″ and 5 position trisubstituted silyl protected hydroxy derivatives thereof.

2. The compound of claim 1 wherein A is a single bond and B is a double bond or an epoxide, C is a double bond and D is a single bond or a double bond;

$R_1$ is hydrogen or hydroxy when D is a single bond;

$R_2$ is methyl, ethyl, isopropyl or see-butyl;

$R_3$ is hydroxy;

$R_4$ is hydrogen, hydroxy, halogen, loweralkoxy, loweralkanoyloxy, 4′-R$_5$-(α-oleandrosyloxy), 4″-R$_5$-[(α-L-oleandrosyl)-α-L-(oleandrosyloxy)];

$R_5$ is hydroxy, amino, loweralkylamino or diloweralkylamino;

$R_8$ is hydrogen, chloro or bromo; and $R_9$ is hydrogen, halogen, hydroxy or oxo.

3. The compound of claim 2 which is 10,11-dihydroavermectin B1a and B1b.

4. The compound of claim 2 which is 10,11,22,23-tetrahydro avermectin B1a and B1b.

5. The compound of claim 2 which is 13-deoxy-10,11,22,23-tetrahydroavermectin B1 1a and B1b aglycone.

6. The compound of claim 2 which is 4″-deoxy-10,11-dihydro-4″-methylamino-10-fluoro avermectin B1a and B1b.

7. The compound of claim 2 which is 4″-methylamino-4″-deoxy-10,11-dihydroavermectin B1a and B1b.

8. The compound of claim 2 which is 10,11-dihydro-10-fluoroavermectin B1a and B1b.

9. A method for the treatment of parasitic infections which comprises administering to an animal infected with parasites an effective amount of a compound of claim 1.

10. A composition useful for treating animals infected with parasites or for treating areas infested with insect pests which comprises an inert carrier and a compound of claim 1.

11. A method for the treatment of insect pests which comprises applying to an area infected with such insect pests, an effective amount of a compound of claim 1.

* * * * *